(12) United States Patent
Gopalakrishnakone et al.

(10) Patent No.: US 7,579,433 B2
(45) Date of Patent: Aug. 25, 2009

(54) METHODS AND COMPOSITIONS FOR TREATMENT OF ARTHRITIS AND CANCER

(75) Inventors: Ponnampalam Gopalakrishnakone, Singapore (SG); Maung-Maung Thwin, Singapore (SG); Kazuki Sato, Fukuoka (JP)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 11/414,719

(22) Filed: Apr. 28, 2006

(65) Prior Publication Data

US 2007/0037253 A1 Feb. 15, 2007

Related U.S. Application Data

(63) Continuation-in-part of application No. 10/836,825, filed on Apr. 30, 2004, now Pat. No. 7,176,281.

(60) Provisional application No. 60/466,421, filed on Apr. 30, 2003.

(51) Int. Cl.
A61K 38/10 (2006.01)
A61K 38/00 (2006.01)
(52) U.S. Cl. .......................................... 530/326; 514/2
(58) Field of Classification Search ........................ None
See application file for complete search history.

(56) References Cited

U.S. PATENT DOCUMENTS 6,498,242 B1 12/2002 Cheng et al.

FOREIGN PATENT DOCUMENTS

WO WO 0142462 A2 6/2001

OTHER PUBLICATIONS

Abstract of: E. Abraham, et al., "Efficacy and Safety of LY315920Na/S-5920, a Selective Inhibitor of 14-kDa Group IIA Secretory Phospholipase A2, in Patients with Suspected Sepsis and Organ Failure", Crit. Care Med., vol. 31, No. 3, pp. 718-728 (2003).
Akhlaq A. Farooqui, et al., "Inhibitors of Intracellular Phospholipase $A_2$ Activity: Their Neurochemical Effects and Therapeutical Importance for Neurological Disorders", Brain Research Bulletin, vol. 49, No. 3, pp. 139-153 (1999).
Akhlaq A. Farooqui, et al., "Involvement of Phospholipase $A_2$ in Neurodegeneration", Neurochem. Int., vol. 30, No. 6., pp. 517-522 (1997).
Abstract of: J. Balsinde, et al., "Regulation and Inhibition of Phospholipase A2", Annu. Rev. Pharmacol. Toxicol., vol. 39 pp. 175-189 (1999).
Abstract of: G. Cirino, et al., "Recombinant Secreted Nonpancreatic Phospholipase A2 Induces a Synovitis-Like Inflammation in the Rat Air Pouch", J Rheumatol, vol. 21, No. 5, pp. 824-829 (1994).

Abstract of: J.A. Green, et al., "Circulating Phospholipase A2 Activity Associated with Sepsis and Septic Shock is Indistinguishable from that Associated with Rheumatoid Arthritis", Inflammation, vol. 15, No. 5, pp. 355-367 (1991).
Omar S. Jamal, et al., "Increased Expression of Human Type IIa Secretory Phospholipase $A_2$ Antigen in Arthitic Synovium", Ann. Rheum. Dis., vol. 57, pp. 550-558 (1998).
Abstract of P. Kortekangas, et al., "Group II Phospholipase A2 in Synovial Fluid and Serum in Acute Arthritis", Scand. J Rheumatol, vol. 23, No. 2, pp. 68-72 (1994).
Abstract of M.K. Lin, et al., "Secretory Phospholipase A2 as an Index of Disease Activity in Rheumatoid Arthritis. Prospective Double Blind Study of 212 Patients", J Rheumatol, vol. 23, No. 7, pp. 1162-1166 (1966).
Xin-Rong Lu, et al., "Differential Effects of Calcium-Dependent and Calcium-Independent Phospholipase A.sub.2 Inhibitors on Kainate-Induced Neuronal Injury in Rat Hippocampal Slices", Free Radical Biology & Medicine, vol. 30, No. 11, pp. 1263-1273 (2001).
Timo J. Nevalainen, et al., "Roles of Secretory Phospholipase $A_2$ in Inflammatory Diseases and Trauma", Biochimica Acta, vol. 1488, Nos. 1-2, pp. 83-90 (2000).
Abstract of: T.J. Nevalainen, et al., "Pancreatic and Synovial Type Phospholipases A2 in Serum Samples from Patients with Severe Acute Pancreatitis", Gut., vol. 34, No. 8, pp. 1133-1136 (1993).

(Continued)

*Primary Examiner*—Maryam Monshipouri
*Assistant Examiner*—Marsha M Tsay
(74) *Attorney, Agent, or Firm*—Townsend and Townsend and Crew LLP (57) ABSTRACT

The present invention provides a new 18-residue homodimerized peptide, designated PIP [59-67] dimer (SEQ ID NO: 1), which is a mutant of the optimized anti-inflammatory peptide P-NT.II, the patent for which has recently been filed [1]. P-NT.II has the potential to modulate both the inflammatory and bone damaging components of rheumatoid arthritis, and was originally designed on the basis of the primary structure of the anti-inflammatory protein termed 'Phospholipase Inhibitor from Python (PIP)' [2]. Using solid phase chemistry, variants of P-NT.II were designed and examined for inhibitory activity against secretory phospholipase A2 (sPLA2), a key enzyme involved in the inflammatory pathway, and matrix metalloproteinases (MMPs) that are involved in the remodeling and degradation of the extracellular matrix in rheumatoid arthritis (RA) and cancer. Among the family of mutants tested, the dimerized peptide was found to be the most potent inhibitor against sPLA2 as well as the human recombinant MMP-1. This invention provides the utility of the peptide analogue PIP [59-67] dimer as a potential therapeutic agent for modulation of inflammatory diseases such as rheumatoid arthritis, and cancer. This invention relates to all the polypeptide analogues (SEQ ID NO: 1 to 3) and polynucleotides (SEQ ID NO: 4), and to the use of those polypeptides and polynucleotides, their synthetic chemical analogues or variants that inhibit activity and synthesis of sPLA2 and MMPs, in the diagnosis, study, prevention and treatment of rheumatoid arthritis and/or cancer.

12 Claims, 4 Drawing Sheets

OTHER PUBLICATIONS

Anna M. Planas, et al., "Induction of Cyclooxygenase-2 mRNA and Protein Following Transient Focal Ischemia in the Rat Brain", Neuroscience Letters, vol. 200, pp. 187-190 (1995).

T.L. Sandhya, et al., "A Light and Electron Microsphere Study of Cytoplasmic Phospholipase $A_2$ and Cyclooxygenase-2 in the Hippocampus after Kainate Lesions", Brain Research, vol. 788, pp. 223-231 (1998).

David W. Snyder, et al., "Pharmacology of LY315920/S-5920,.sup.1 [[3-(Aminooxacetyl)-2-ethyl-1-(phenylmethyl)-1H-indol-4-yl]oxy]acetate, a Potent and Selective Secretory Phospholipase $A_2$ inhibitor: A New Class of Anti-Inflammatory Drugs, SPI", The Journal of Pharmacology and Experimental Therapeutics, vol. 288, No. 3, pp. 1117-1124 (1999).

L. Stoppini, et al., "A Simple Method for Organotypic Cultures of Nervous Tissues", Journal of Neuroscience Methods, vol. 37, pp. 173-182 (1991).

Muang-Maung Thwin, et al., "Functional Site of Endogenous Phospholipase $A_2$ Inhibitor from Python Serum, Phospholipase $A_2$ Binding and Anti-Inflammatory Activity", Eur. J. Biochem., vol. 269, pp. 719-727 (2002).

M.-M. Thwin, et al., "Recombinant Antitoxic and Antiinflammatory Factor from the Nonvenomous Snake Python reticulatus: Phospholipase $A_2$ Inhibition and Venom Neutralizing Potential", Biochemistry, vol. 39, pp. 9604-9611 (2000).

Thwin, M.M., et al. 2000 Chemistry 39: 9604-9611.

Abstract of P. Vadas, et al., "Induction of Group II Phospholipase A2 Expression and Pathogenesis of the Sepsis Syndrome", Circ. Shock., vol. 39, No. 2, pp. 160-167 (1993).

Tatsurou Yagami et al., "Human Group IIA Secretory Phospholipase $A_2$ Induces Neuronal Cell Death via Apoptosis", Molecular Pharmacology, vol. 61, No. 1, pp. 114-126 (2002).

METHODS AND COMPOSITIONS FOR TREATMENT OF ARTHRITIS AND CANCER

CROSS-REFERENCE TO RELATED APPLICATIONS

This is a Continuation In Part of U.S. patent application Ser. No. 10/836,825, filed Apr. 30, 2004, now U.S. Pat. No. 7,176,281, which claims the benefit of U.S. Provisional Patent Application Ser. No. 60/466,421, filed Apr. 30, 2003. The contents of both of these Applications are hereby incorporated by reference in their entirety.

FIELD OF THE INVENTION

The present invention pertains to a novel 18-residue dimerized peptide designated PIP [59-67] dimer, having dual inhibitory activity against secretory phospholipase A2 (sPLA2) and matrix metalloproteinases (MMPs). This novel peptide inhibitor of the invention not only inhibits the enzymatic activity of sPLA2 and MMPs, but also downregulates their mRNA expression and hence protein synthesis. The invention also provides utility of this peptide PIP [59-67] dimer, its synthetic chemical analogues or polypeptide variants as potential therapeutic/prophylactic drug against rheumatoid arthritis (RA) and the use of such agents in connection with the treatment of cancer.

All documents cited in this text ("herein cited documents") and all documents cited or referenced in herein cited documents and sequences from GenBank and other data bases referred to herein are incorporated by reference in their entirety for all purposes.

There is no admission that any of the various documents etc. cited in this text are prior art as to the present invention.

BACKGROUND

Phospholipase $A_2$ ($PLA_2$) is a key enzyme in the production of diverse mediators of inflammatory conditions, and is implicated in the pathophysiology of many diseases including arthritis, cancer, inflammatory bowel diseases, sepsis, septic shock, pancreatitis, stroke and post-surgical peritoneal adhesions. Correlation to $PLA_2$ activity has furthermore been observed with several forms of acute and chronic brain injury, including cerebral trauma, ischemic damage, induced seizures in the brain and epilepsy, schizophrenia, and in particular, Alzheimer's disease (AD) [25]. The vast $PLA_2$ enzyme family includes three cellular isoforms ($cPLA_2s$), involved in signal transduction, and ten secretory isoforms ($sPLA_2s$). The $cPLA_2s$ and $sPLA_2$ play key roles in arachidonic acid (AA) release during acute inflammation [1]. Group IIA secretory phospholipase ($sPLA_2s$-IIA) is known to be proinflammatory in vivo [2], and is associated with the onset of rheumatoid arthritis (RA) [3] Levels of $sPLA_2$ in synovial fluid also correlate with severity of disease in RA patients [4]. Hence, inhibition of $sPLA_2$ may logically block the formation of a wide variety of secondary inflammatory mediators. Moreover, sPLA2 is known as an important amplifier of cytokine-mediated prostaglandin (PG) production, and as such it plays a central role in tumour development and progression [5, 6]. Tumors from human and experimental animals produce large quantities of prostaglandins [7], which can modulate the interaction of tumor cells with various host components in cancer metastasis. Supplying $PLA_2$ inhibitors to the cancerous tissues will therefore inhibit $sPLA_2$ activity and reduce cyclooxygenase-2 (COX-2) expression, which in turn will suppress the catalytic conversion of arachidonic acid (AA) to PGE. This would interfere with metastasis and growth of neoplastic cells. The central role of sPLA2 in inflammatory arthritis and cancer thus makes the enzyme a potential target for drug development. It has long been recognized that inhibition of phospholipase $A_2$ ($PLA_2$)-catalyzed arachidonic acid (AA) release from cell-membrane glycerophospholipids could potentially block the synthesis of all eicosanoids, but this is yet to be realized.

In our previous patent filing [8] we have shown that $sPLA_2$-IIA is inhibited by various peptide sequences derived by us from the native $PLA_2$-inhibitory protein termed "Phospholipase Inhibitor from Python (PIP)" [9]. We have recently found that a new peptide sequence resulting from further screening of the PIP to generate inhibitors with improved potency is effective at lower micromolar concentrations in inhibiting $sPLA_2$-IIA enzyme activity [10], and $sPLA_2$-mediated amplification of cytokine-induced prostaglandin synthesis in mouse macrophage J774 cells in culture [11]. This new inhibitory peptide is specific and selective for $sPLA_2$ [12]. Our in vivo experiment with transgenic mice overexpressing human TNFα further confirms the prophylactic effectiveness of this novel peptide against inflammatory arthritis in a chronic autoimmune inflammatory process [11, 13]. Despite numerous studies and accumulation of data on $PLA_2$ inhibitors, there are no effective inhibitors presently available for clinical use either as anti-inflammatory or as anticancer agents. To date, only a few $PLA_2$ inhibitors have progressed into clinical trials as potential drug candidates for inflammatory diseases, and unlike this short peptide they are all but organic compounds. Moreover, no $sPLA_2$ inhibitory peptides have so far been available as drug candidates for rheumatoid arthritis (RA) or cancer treatment.

Besides the involvement of $sPLA_2$ in RA, matrix metalloproteinases (MMPs), the zinc- and calcium-dependent family of proteins produced by synovial fibroblasts, chondrocytes, and infiltrating leukocytes [14], have been implicated in the collagen breakdown that contributes to joint destruction in RA. Several different MMPs have been shown to be present in the joints of RA patients [15]. An imbalance between the active enzymes and their natural endogenous inhibitors known as 'Tissue Inhibitors of Metallo-Proteinases (TIMPs)' leads to the accelerated destruction of connective tissue, which is associated with the pathology of diseases such as arthritis, cancer, multiple sclerosis and cardiovascular diseases [16]. Collagenase (MMP-1) and gelatinases (MMP-2 and MMP-9) are implicated in cancer and their inhibition has therefore been suggested as a therapeutic option [17, 18]. Accordingly, the inhibition of MMP synthesis and/or activity represents novel potential therapeutic strategies for the treatment of cancer. The potential for using specific enzyme inhibitors as therapeutic agents has therefore led to intensive research focused on the design, synthesis and molecular deciphering of low-molecular-mass inhibitors of this family of proteins. Supported by X-ray and NMR data on MMP complexes, and by exploiting sequence and structural differences in the principal specificity pocket of the enzymes, subtype-selective MMP inhibitors have been designed [19]. However, despite promising results seen in animal models, clinical trials with MMP inhibitors in cancer patients have been disappointing so far [18, 20]. Hence, the use of dual inhibitors against $sPLA_2$ and MMPs, and in early stages of disease onset, could be a novel approach geared towards achieving improved clinical advantage over the use of MMP inhibitors alone in the treatment of cancer.

OBJECTIVES OF THE INVENTION

Various goals intended to be achieved: Utility of the 18-residue peptide PIP [59-67] dimer, its synthetic chemical analogues or polypeptide variants as potential therapeutic/prophylactic drug against rheumatoid arthritis (RA) and cancer.

Problems that can be solved & the advantages over existing materials: With respect to anti-inflammatory drugs, non-steroidal aspirin-like anti-inflammatory drugs (NSAIDs) have been the mainstay of the treatment of rheumatoid and other forms of arthritis, but these drugs only relieve symptoms such as pain and swelling without changing the course of underlying disease. Immunosuppressants such as cyclosporine or anti-metabolite drugs such as methotrexate are effective but have dose-limiting adverse effects. Biologicals such as monoclonal antibodies or immuno-fusion proteins are on the market or in development, but there are problems with respect to immune responses, since they are large protein molecules. One of the cardinal manifestations of rheumatoid arthritis is joint destruction due mainly to destruction of bone matrix by various matrix metalloproteinases (MMPs) released during the disease process, and the inhibition of these enzymes thus represents a further strategy in the treatment of rheumatoid arthritis. Our innovation has a competitive advantage as the peptide has the capacity of targeting these MMPs, besides its suppressive activity against bone erosion and cartilage destruction through sPLA2 inhibition. Moreover, recent approval of therapeutic peptide products in therapeutic areas indicates that peptides are viable options as therapeutic molecules. The commercial viability of peptides through their ease in synthesis and delivery at a relatively lower-cost compared with other anti-inflammatory and anti-cancer drugs will create competitive advantage for the treatment of these diseases.

Possible industrial applications: As potential therapeutic or prophylactic agent for the treatment of rheumatoid arthritis, cancer, inflammation or any conditions associated with the activity and/or expression of sPLA2 and MMPs.

Disadvantages or limitations: We have used intraperitoneal route of administration for testing the efficacy of peptides in animal models, and have yet to examine the oral treatment, which is presumed to be the best and easiest way of giving a drug to a patient. The limitation for successful oral treatment appears to be potential peptide instability towards gastrointestinal proteolytic enzymes. This can be overcome through cyclization and replacement of L-amino acids with D-amino acids.

SUMMARY OF INVENTION

This invention is based on the fact that small molecule peptides having dual activity against the secretory phospholipase A2 (sPLA2) and matrix metalloproteinases (MMPs) may confer a therapeutic benefit over the use of inhibitors having single activity against sPLA2 or MMP. We have recently synthesized analogues of the lead sPLA$_2$ inhibitor peptide that we previously designed, and examined them for MMP inhibitory activity. Among the family of mutants tested, the dimerized peptide was found to be the most potent inhibitor against the human recombinant MMP-1. When the effects of peptide mutants on the secretion of matrix metalloproteinases (MMPs) from rabbit synovial fibroblasts were examined, the dimer markedly inhibited the enzyme activity of MMP-1, secreted from IL-1 β-stimulated rabbit synovial fibroblasts, while inhibition of the activity of other secreted MMPs (proMMP-2, MMP-2, proMMP-9 and MMP-9) was less marked. Furthermore, mRNA expression of MMP-1, MMP-2, MMP-9 and sPLA$_2$ was found to be significantly decreased (>1-fold) after treatment of the IL-1β-stimulated rabbit synovial fibroblasts with the dimerized peptide in culture. Our results strongly indicate that sPLA$_2$-inhibitory peptides that we have designed may be therapeutically effective inhibitor of matrix-degrading enzymes. The optimized peptide analogue presents strong in vitro evidence for control and modulation of enzyme activity and/or transcription of both MMP and sPLA$_2$, and provides new therapeutic options in the treatment of arthritis and cancer.

The 18-residue dimerized peptide PIP [59-67] dimer, and the amino acid sequences of peptide analogues, of which are herein referred to as SEQ ID NO: 1 to 3, and any synthetic chemical analogues or polypeptide variants or any other similar sequences or portions thereof, produced by means of synthetic chemistry, are related to the present invention and can be used for the study, prevention and treatment of inflammatory diseases, particularly rheumatoid arthritis, and of cancer. Preferred embodiments are given in the dependent claim 1 to 4.

The present invention provides a new 18-residue homodimerized peptide, designated PIP [59-67] dimer (SEQ ID NO: 1), which is a mutant of the optimized anti-inflammatory peptide P-NT.II, the patent for which has recently been filed [1]. P-NT.II has the potential to modulate both the inflammatory and bone damaging components of rheumatoid arthritis, and was originally designed on the basis of the primary structure of the anti-inflammatory protein termed 'Phospholipase Inhibitor from Python (PIP)' [2]. Using solid-phase chemistry, variants of P-NT.II were designed and examined for inhibitory activity against secretory phospholipase A2 (sPLA2), a key enzyme involved in the inflammatory athway, and matrix metalloproteinases (MMPs) that are involved in the remodeling and degradation of the extracellular matrix in rheumatoid arthritis (RA) and cancer. Among the family of mutants tested, the dimerized peptide was found to be the most potent inhibitor against sPLA2 as well as the human recombinant MMP-1. This invention provides the utility of the peptide analogue PIP [59-67] dimer as a potential therapeutic agent for modulation of inflammatory diseases such as rheumatoid arthritis, and cancer. This invention relates to all the polypeptide analogues (SEQ ID NO: 1 to 3) and polynucleotides (SEQ ID NO: 4 to 6), and to the use of those polypeptides and polynucleotides, their synthetic chemical analogues or variants that inhibit activity and synthesis of sPLA2 and MMPs, in the diagnosis, study, prevention and treatment of rheumatoid arthritis and/or cancer.

BRIEF DESCRIPTION OF DRAWINGS

Various aspects of the invention and its relationship to the prior art will be described with reference to the accompanying drawings, in which:

[59-67] monomer; lanes 7-8: 10, 5 μM LY315920; lane 9: control (without inhibitor). (B) The mean density (OD/mm2) ±SD (n=3), representing MMP-2 activity, obtained by scanning the zymograms using the GS-710 calibrated imaging densitometer (Bio Rad, USA). For each type of treatment, Student's t-test did not show any significant difference from the control (P>0.05).

FIG. 4 shows the effect of inhibitors on gelatinase (MMP-9 and MMP-2) activity in the supernatant of cultured rabbit synoviocytes (HIG-82). Gelatinase activity in the supernatants from cells induced with IL-1β (5 ng) for 48 h was analyzed by gelatin zymography. (A) Supernatants (activated with final 1 mM APMA at 30° C. for 30 min) were pre-incubated with various inhibitors. (5 μM peptides or 1-2 μM Calbiochem MMP inhibitor II) for 1 h at 25° C. prior to zymographic analyses—Lane 1, without activation (no inhibitor); Lane 2, with activation (no inhibitor); Lanes 3-8, with activation plus inhibitor: 3, P-NT-II; 4, PIP [59-67] monomer; 5, PIP [57-67] dimer; 6, PIP [59-67] dimer; 7 and 8, positive control MMP Inhibitor II (Calbiochem) at 1 and 2 μM concentrations. (B) Rabbit synovial fibroblasts were stimulated by IL-1β in the presence or absence of 1-10 μM of PIP [59-67] dimer for 48 h. Culture supernatants were concentrated by centrifugation (Centricon centrifugal filter devices, M.W. cutoff 30,000) and activated with APMA (1 mM final) before measurement of gelatinase activity by gelatin zymography. Lanes: 1 (−peptide−APMA); 2 (−peptide+ APMA); 3 (+1 μM peptide+APMA); 4 (+5 μM peptide+ APMA); 5 (+7.5 μM peptide+APMA); 6 (+10 μM peptide+ APMA).

GLOSSARY OF TERMS

This section is intended to provide guidance on the interpretation of the words and phrases set forth below (and where appropriate grammatical variants thereof). Further guidance on the interpretation of certain words and phrases as used herein (and where appropriate grammatical variants thereof) may additionally be found in other sections of this specification.

As used in this application, the singular form "a," "an," and "the" include plural references unless the context clearly dictates otherwise. For example, the term "an agent" includes a plurality of agents, including mixtures thereof.

As used herein, the term "comprising" means "including." Variations of the word "comprising", such as "comprise" and "comprises," have correspondingly varied meanings. Thus, for example, a composition "comprising" X may consist exclusively of X or may include one or more additional components.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers with in that range, for example, 1, 2, 3, 4, 5, and 6. This applies regardless of the breadth of the range.

Unless otherwise indicated, all technical and scientific terms used herein have the same meaning as commonly understood to one of ordinary skill in the art to which the invention belongs.

DETAILED DESCRIPTION

The practice of the present invention will employ, unless otherwise indicated, conventional techniques of molecular biology, microbiology, and recombinant DNA technology which are within the skill of those working in the art. Such techniques are explained fully in the literature. Examples of texts for consultation include the following: Sambrook Molecular Cloning; A Laboratory Manual, Third Edition (2000).

Included within the scope of the present invention are those sequences and fragments of the polypeptides as described in SEQ ID NO: 1 to 3, or functional equivalents thereof, which can be used for treating or preventing inflammatory conditions, especially in rheumatoid arthritis, and as potential anticancer drug. In yet another aspect, the invention contemplates a method of producing a polypeptide variant of a parent polypeptide comprising the sequences set forth in SEQ ID No: 1-3, or biologically active fragments thereof, comprising the steps of:

(a) Replacing at least one amino acid of the parent polypeptide, with a different amino acid to produce a modified polypeptide;

(b) Deleting and/or adding the parent polypeptide, modifying the side chains, incorporating unnatural amino acids and/or their derivatives during peptide, polypeptide synthesis and the use of crosslinkers and other methods which impose conformational constraints on the polypeptides, fragments and variants of the invention;
(c) Modifying the polypeptides, fragments or variants of the invention using ordinary molecular biology techniques to improve their resistance to proteolytic degradation or to optimize solubility properties or to render them more suitable as an immunogenic agent.

EXAMPLES

The described features of the invention can be gathered from the following description of preferred embodiments in conjunction with the claims. The inventors have discovered the new peptide analogue with dual inhibitory activity against sPLA2 and MMPs by using the following materials and methods:

Synthesis and Characterization of sPLA$_2$ Inhibitory Peptides

A family of peptides was synthesized based on the sequence of PIP (Thwin et al. 2000; GenBank Accession Nos. AAF73945, AX175043, CAC43861, CAC43862, CAC43863) using the solid phase method with 9-fluorenylmethoxy carbonyl chemistry. The peptides were purified by successive chromatography with gel filtration and reverse phase high pressure liquid chromatography to more than 95% purity with yields between 10-30%. The sequences were validated by matrix-assisted laser desorption/ionization time-of-flight mass spectrometry (MALDI-TOF-MS).

Determination of PLA$_2$ Inhibitory Activity

This was carried out as described previously [10]. In brief, [$^3$H] arachidonate-labeled *E. coli* membranes (0.005 mCi/mL; 5.8 µCi/µmol, NEN) were used as substrate, and 100 mM Tris-HCl—25 mM CaCl$_2$, pH 7.5 solution as an assay buffer. The reaction mixture contained 20 µL of substrate, 0.85 pmole of purified human synovial sPLA$_2$ (human Type IIA sPLA$_2$, Cayman Chemicals, USA), and an increasing concentrations of the family of synthetic peptides derived from the sequence of PIP. The final volume of the reaction mixture was adjusted to 250 µL with an assay buffer. After incubation of the mixture (37° C., 1 h) and termination of the reaction with 750 µL of chilled PBS containing 1% BSA, microfuge tubes containing the samples were centrifuged (10,000 g at 4° C. for 15 min), and 500 µL aliquots of the supernatant taken to measure the amount of [$^3$H]-labeled arachidonate released from the *E. coli* membrane using liquid scintillation counting (Multipurpose Scintillation Counter LS 6500; Beckman, USA). As controls, sPLA$_2$ was pre-incubated with the assay buffer alone. All samples, including controls, were performed in triplicate and plotted as the percentage inhibition relative to negative controls.

IC$_{50}$ Determination

IC$_{50}$ was determined by pre-incubating varying concentrations (1-250 µM) of inhibitors in a constant volume, against a constant amount of enzyme as described earlier. A sigmoid dose response curve was generated to allow calculation of the IC$_{50}$ values. All samples were performed in triplicate. Results were analyzed by nonlinear regression with GraphPad Prism (version 2.01) and expressed as the percentage of inhibition relative to control values.

Gelatin zymography: human synovial fluid, purified human recombinant MMP-2 and -9 or APMA-activated concentrated culture supernatant samples (10 µL) was mixed (1:1) with Laemmli sample buffer, loaded on 4% acrylamide stacking gel and electrophoresed (120 V) at 4° C. on a 10% acrylamide-resolving minigel containing 0.1% gelatin. After electrophoresis for 1 h, the gels were soaked in 2.5% Triton X-100 on a shaker for 1 h, changing the solution after 30 min, to eliminate SDS. After overnight incubation in zymogen activation buffer [50 mM Tris-HCl, pH 7.5, containing 10 mM CaCl$_2$ and 5 mM ZnCl$_2$] at 37° C., the gels were rinsed in distilled water, and stained for 3 hr with Bromphenol blue, after which clear bands of digested gelatin were clearly visible. The gels were briefly rinsed in distilled water and scanned by the Bio-Rad GS-710 Calibrated Imaging Densitometer.

Collagenase activity assay: Using collagen thin film as the substrate, a quantitative method [21] was established to measure the enzymatic activity of the MMPs (principally collagenase). Collagen type II (Sigma) solution (4 µL, 3 mg/mL in 0.012 N HCl) was added to each well of 96-well plates and precipitated by slowly increasing the pH with 4 µL of H$_2$O and 8 µL of 0.012 N NaOH. The plate was dried at 23° C. for 24 hr, washed with H$_2$O, and dried again at 23° C., resulting in a thin film containing 12 µg of collagen that was tightly bound to the bottom of the wells. Enzymatic reactions of the collagenase I (with and without peptide inhibitors) against the collagen films were carried out in quadruplicate at 24° C. for 16 h. The digested portion of the film was washed away, while the undigested portion was fixed for 3 h with 0.1% Coomassie brilliant blue R in 10% acetic acid and 45% methanol, and the wells washed and dried. The undigested film was then dissolved in 100 µL of ethanol for 20 min to obtain a uniform colour distribution, and the OD of each well read with a Molecular Devices E$_{max}$ precision microplate reader at 595 nm.

Inhibition of MMP-1 enzymatic activity: Enzyme inhibition by peptide analogues was assessed by using MMP-1 Colorimetric assay kit for drug discovery (BIOMOL AK-404 QuantiZyme Assay system). Briefly, human recombinant MMP-1 catalytic domain in each well (15.3 U, 20 µL) was allowed to react either with the candidate peptide (test inhibitor) dissolved in DMSO (final 0.5% DMSO in assay buffer), or with the assay buffer alone (control) for 30 min at 37° C. Immediately following incubation, the reaction was initiated by adding the thiopeptide substrate solution in assay buffer (10 µL of 100 µM Ac-PLG-[2-mercapto-4-methyl-pentanoyl]-LG-OC$_2$H$_5$) into each well, and the absorbance at 412 nm continuously monitored for 10 min. 1 mM Ellman's reagent [5,5'-dithiobis (2-nitrobenzoic acid] in assay buffer (50 mM HEPES, 10 mM CaCl2, 0.05% Brij-35) was used as a colour developer in this assay system. The reaction velocity (V) was determined from the slope of the OD versus time (min) plot for each test inhibitor using the linear regression analysis (Graph Pad Prism, Version 2). Inhibition (%) was then calculated using the equation, [100]−[(V inhibitor/V control)×100].

FLSC culture and inhibition of extracellular MMP activity: All experiments were performed on HIG-82 rabbit fibroblast-like synoviocytes (FLSCs) obtained from American Type Culture Collection (Manassas, Va.; catalogue No. CRL-1832). FLSCs were grown in Ham's F-12 medium containing 10% fetal bovine serum (FBS) and 1% penicillin/streptomycin, as recommended by the supplier. For experimental purposes, FLSCs were seeded into 12-well plates, grown to near confluence, and then serum starved (Ham's F-12 without FBS or penicillin/streptomycin) for 16 h. After serum starvation of FLSCs, supernatants were removed and replaced with fresh Ham's F-12 medium for 60 min at 37° C./5% CO$_2$ before incubation for 2 h with various concentrations (1-10 µM) of test inhibitor peptides: P-NT.II, PIP [59-67] monomer and dimer. FLSCs were then stimulated for 24 h with IL-1β (10 ng/mL), and the supernatants concentrated by centrifugation in Centricon centrifugal filter devices (M.W. cutoff 30,000) for 35 min at 5000 rpm at 4° C. After activation with APMA (1 mM final concentration), the samples were measured for MMP-1 activity using BIOMOL AK-404 QuantiZyme Assay system, and for MMP-2 and -9 activities by gelatin zymography.

Cell viability assays: XTT (Sodium 3'-[Phenyl amine carboxyl)-3,4-tetrazolium]-bis(4-methoxy-nitro) benzene sulfonic acid hydrate) Cell Proliferation Kit II (Roche Applied Science) was used to assess the possible cytotoxic effect of the peptides on the rabbit FLSCs.

RNA isolation of cultured FLSCs: FLSCs were grown to 80% confluence on 12-well culture dishes and starved in a serum-free medium with 5 µM PIP [59-67] dimer for 2 h. The cells were then stimulated with 5 ng/mL IL-1β (Recombinant human, Chemicon, USA.) for 24 h, washed with cold PBS and total RNA isolated from peptide-treated (n=3) and untreated (n=3) FLSCs using RNeasy® mini kit. The RNA samples were subsequently treated with RNase-free Dnase-I at room temperature for 20 min and stored at −80° C. until use. The quality and quantity of extracted RNA was determined by spectrophotometry (Bio-Rad, USA). All RNA samples used for QRT-PCR experiments were of highest purity with $A_{260}/A_{280}$ ratios of 1.9-2.1. The integrity and relative contamination with residual genomic DNA was assessed by 1% denaturing agarose gel electrophoresis.

Quantitative Real Time RT-PCR (LightCycler): Quantitative fluorescence-based real-time PCR was carried out according to the manufacturer's instructions using the LightCycler system with LightCycler FastStart DNA Master$^{PLUS}$ SYBR Green I kit (Roche Diagnostics, Germany) as an independent method for assessing relative gene expression. Reverse Transcription (RT) of RNA and QRT-PCR were performed as follows: single stranded cDNA was generated from 3 µg of total RNA, 200 µM nucleotides, 500 units Superscript II reverse transcriptase (Invitrogen) and 1.5 µM oligo(dT)$_{15}$ primers in 50 µL reactions. Reverse transcription was stopped after 1 hr by heating to 95° C. for 5 min. The sense and anti-sense primers used for specific amplification and conditions for PCR cycles are shown in Table 1. The primers were designed by Primer3 software: http://bioinformatics.weizmann.ac.il/cgi-bin/primer/primer3.cgi and subsequently checked for specificity using BLAST: http://www.ncbi.nlm.nih.gov/genome/seq/HsBlast.htmL. All primers and probes were synthesized by 1$^{st}$ BASE Pvt. Ltd., Singapore. The expression of GAPDH was used as an internal calibrator for equal RNA loading and to normalize relative expression data for all other genes analyzed. The copy ratio of each analyzed cDNA was determined as the mean of 3 experiments. The real-time quantitative RT-PCR data were quantified using relative quantification ($2^{-\Delta\Delta C}T$) method as described [Livak, K. J, and Schmittgen, T. D. (2001) Analysis of relative gene expression data using real-time quantitative PCR and the 2(-Delta Delta C(T)) method [22].

RESULTS

Based on in vitro inhibition assays against a purified human synovial sPLA$_2$ (Cayman, USA), P-NT.II analogue, PIP [59-67] monomer, was identified as the shortest peptide possessing strongest sPLA$_2$-inhibitory activity (IC$_{50}$ 3.8 µM). Displacing Asp (D) with Ala (A), Ser (S) or Glu (E) did not significantly enhance the inhibitory potency. However, a homodimer of PIP [59-67] resulted in significant enhancement in sPLA$_2$ inhibitory activity (IC$_{50}$ 1.19 µM). The results (Table 1) indicate that the dimerized peptide, PIP [59-67] dimer, has the strongest inhibitory activity against the purified human synovial sPLA2, while the other mutants are relatively less potent.

The instability index shown in Table 2 indicates that the peptide mutant D60, 65E-PIP [59-67] monomer may not be as stable as the other mutants, PIP [59-67] monomer or the dimer, because of the former having an index greater than 40. Both the dimers of PIP[59-67] and PIP [57-67] appear to be more stable based on their instability indices (i.e., 6.46 and 3.2, respectively), but PIP [57-67] dimer has a shorter half life compared to that of PIP [59-67] dimer, and as a result PIP [59-67] dimer may be the inhibitor of choice for therapeutic purposes.

Figure 1:
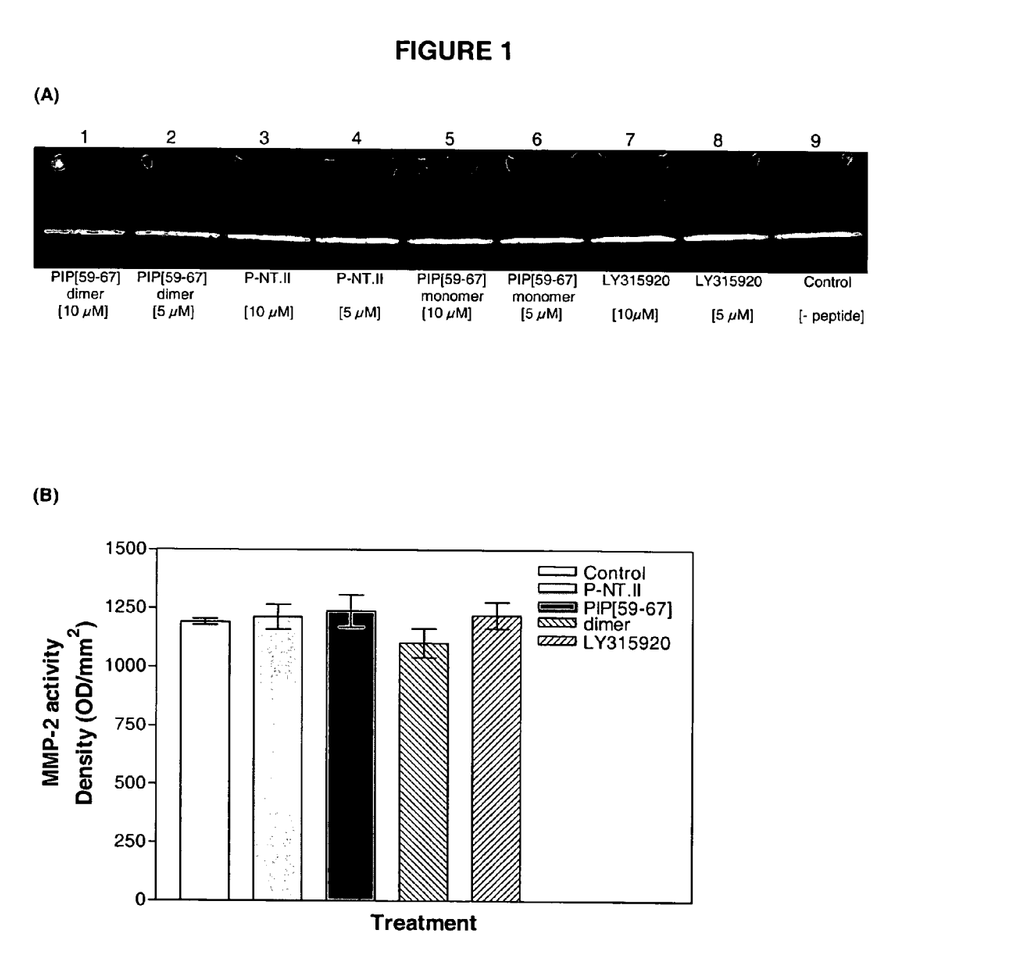
FIG. 1 shows the zymographic analysis of gelatinases (MMP-2, -9) in human synovial fluid samples. (A) Samples containing human synovial fluid (5 µL) and 5 or 10 µM of peptides were pre-incubated at 37° C. for 1 h in Tris-HCl buffer prior to electrophoresis on 10% SDS-PAGE gel containing gelatin (0.1%). Lanes 1-2: 10, 5 µM PIP [59-67] dimer; lanes 3-4: 10, 5 µM P-NT.II; lanes 5 -6, 10, 5µM PIP

Since the gelatinases (MMP-2 and MMP-9) play an important role in inflammation, we first tested for inhibition of gelatinase activity using gelatin zymography (FIG. 1A). Zymogram gels were scanned by the GS-710 calibrated imaging densitometer (Bio Rad, USA). Data representing mean±SD (n=3) are not significantly different from control (P<0.05) using Student's t test (FIG. 1B). Since the results indicate that inhibition of the peptides against the gelatinase activity is insignificant, the peptides were examined for inhibition against collagenase activity using purified collagenase I (Sigma) and purified collagen type II (Sigma), in a collagen film assay with some modifications.

TABLE 1

Polypeptide variants of the sPLA2-inhibitory peptide PIP [59-67]

| Polypeptide No. variants | SEQ ID NO: | Sequence | Mol. Wt. | % Inhibition* (mean ± SD) | IC$_{50}$ [µM]$^{\#}$ (mean ± SD) |
|---|---|---|---|---|---|
| 1 PIP [59-67]monomer | 7 | VDIHVW(D)GV (residues 1-9 of SEQ ID NO:1) | 1039 | 56.37 ± 3.21 | 3.80 ± 1.06 |
| 2 D65A-PIP [59-67] | 7 | VDIHVW(A)GV variant of residues 1-9 of SEQ ID NO:1 with D7 → A) | 995 | 48.52 ± 2.34 | 5.45 ± 1.98 |
| 3 D65E-PIP [59-67] | 7 | VDIHVW(E)GV variant of residues 1-9 of SEQ ID NO:1 with D7 → E) | 1053 | 57.62 ± 3.22 | 4.95 ± 2.22 |
| 4 D65S-PIP [59-67] | 7 | VDIHVW(S)GV (variant of residues 1-9 of SEQ ID NO:1 with D7 → S) | 1011 | 52.55 ± 1.08 | 5.25 ± 3.21 |

TABLE 1-continued

Polypeptide variants of the sPLA2-inhibitory peptide PIP [59-67]

| No. | Polypeptide variants | SEQ ID NO: | Sequence | Mol. Wt. | % Inhibition* (mean ± SD) | IC$_{50}$ [µM]$^\#$ (mean ± SD) |
|---|---|---|---|---|---|---|
| 5 | β-Asp65-PIP [59-67] | 7 | VDIHVW(βD)GV variant of residues of 1-9 of SEQ ID NO:1 with D7 → βD | 1039 | 49.71 ± 3.01 | NA |
| 6 | D60,65E-PIP [59-67] | 8 | VEIHVW(E)GV (residues 1-9 of SEQ ID NO:2) | 1067 | 61.42 ± 4.32 | 4.20 ± 2.98 |
| 7 | PIP [59-67]dimer | 1 | VDIHVWDGVVDIHVWDGV (SEQ ID NO:1) | 2060 | 74.55 ± 4.21 | 1.19 ± 0.55 |
| 8 | PIP [57-67]dimer | 20 | GRVDIHVWDGVGRVDIHVWDGV (dimer of residues 1-11 of SEQ ID NO:3) | 2487 | 76.37 ± 3.87 | 2.43 ± 0.76 |
| 9 | D60,65E-PIP [59-67] dimer | 8 | VEIHVWEGVVEIHVWEGV dimer of residues 1-9 of SEQ ID NO:2) | 2116 | 68.54 ± 3.94 | 4.23 ± 0.67 |

*% inhibition determined against purified human synovial sPLA$_2$ (Cayman, USA) at a fixed peptide concentration (5 µM) using $^3$H-labelled *E. coli* membrane assay. Peptide showing the highest inhibitory potency is highlighted.
$^\#$IC$_{50}$ (mean ± SD), half-maximal inhibition concentration [µM] determined from sigmoid inhibition curves (Gradpad Prism).

[Note: As IC$_{50}$ values were calculated based on the results of our assay system using $^3$H-labelled *E coli* membrane as substrate, they can vary depending on the type of method used for measuring the PLA$_2$ activity. Using a chromogenic isolated enzyme assay, LY315920, the first potent and selective sPLA$_2$ inhibitor developed by Eli Lilly Research Laboratories, USA, inhibited sPLA2 activity with an IC$_{50}$ of 9 nM [23], whereas in our assay system, its IC50 was calculated as 2.29 µM].

TABLE 2

Calculated physical properties* of polypeptide variants

| No. | Polypeptide variants | Length (residues) | Isoelectric Point (pI)* | Instability Index$^\dagger$ | t$_{1/2}$~ (h) |
|---|---|---|---|---|---|
| 1 | PIP [59-67] | 9 | 4.20 | 5.90 | 100 |
| 2 | D65A-PIP [59-67] | 9 | 5.08 | -10.80 | 100 |
| 3 | D65E-PIP [59-67] | 9 | 4.35 | 5.90 | 100 |
| 4 | D65S-PIP [59-67] | 9 | 5.08 | 5.90 | 100 |
| 5 | β-Asp65-PIP [59-67] | 9 | 4.20 | 5.90 | 100 |
| 6 | D60, 65E-PIP [59-67] | 9 | 4.51 | 44.00 | 100 |
| 7 | PIP [59-67] dimer | 18 | 4.13 | 6.46 | 100 |
| 8 | PIP [57-67] dimer | 22 | 5.20 | 3.24 | 30 |
| 9 | P-NT.II | 17 | 8.75 | -1.60 | 5.5 |

The dimerized peptide with the strongest sPLA2-inhibitory activity is highlighted.
*Physical properties were calculated using eXpasY ProtParam TOOL;
~Half-life (t$_{1/2}$) calculated according to Gonda D. K. et al (1989) J. Biol. Chem. 264: 16700-12 [6].
Note:
t$_{1/2}$ of PIP [57-67] dimer << PIP [59-67] dimer.
$^\dagger$Instability index calculated according to Guruprasad K. et al.(1990) Protein Engineering 4: 155-61 [7] (Index<40 is predicted as stable).

TABLE 3 (A)

Inhibition of collagenase enzyme activity by P-NT.II analogues

| No. | Peptide Analogues | SEQ ID NO: | Sequence | Collagenase (% Inhibition) | Mol. Wt. |
|---|---|---|---|---|---|
| 1 | P-NT.II | 9 | $^{56}$LGRVDIHVWDGVYIRGR$^{72}$ (variant of residues 1-11 of SEQ ID NO:3, addition of L before residue G1 and addition of YIRGR after residue V11) | 64.2 ± 5.6 | 2011 |
| 2 | PIP [57-72] | 10 | $^{57}$GRVDIHVWDGVYIRGR$^{72}$ (variant of residues 1-11 of SEQ ID NO:3, addition of residues YIRGR after residue V11) | 39.8 ± 3.5 | 1898 |
| 3 | PIP [58-72] | 11 | $^{58}$RVDIHVWDGVYIRGR$^{72}$ (variant of residues 2-11 of SEQ ID NO:3, addition of residues YIRGR after residue V11) | 23.3 ± 2.9 | 1841 |

TABLE 3(A)-continued

Inhibition of collagenase enzyme activity by P-NT.II analogues

| Peptide No. Analogues | SEQ ID NO: | Sequence | Collagenase (% Inhibition) | Mol. Wt. |
|---|---|---|---|---|
| 4 PIP [59-72] | 12 | $^{59}$VDIHVWDGVYIRGR$^{72}$ (variant of residues 3-11 of SEQ ID NO:3, addition of residues YIRGR after residue V11) | 14.5 ± 2.4 | 1684 |
| 5 PIP [60-72] | 13 | $^{60}$DIHVWDGVYIRGR$^{72}$ (variant of residues 4-11 of SEQ ID NO:3, addition of residues YIRGR after residue V11) | ND | 1585 |
| 6 PIP [61-72] | 14 | $^{61}$IHVWDGVYIRGR$^{72}$ (variant of residues 5-11 of SEQ ID NO:3, addition of residues YIRGR after residue V11) | ND | 1470 |

1 versus 2, 3, 4 = significantly different (P < 0.05).
ND = not done.

| No. | Peptide Analogues | SEQ ID NO: | Sequence | Collagenase (% Inhibition) | Mol. Wt. |
|---|---|---|---|---|---|
| 1 | P-NT.II | 9 | $^{56}$LGRVDIHVWDGVYIRGR $^{72}$(variant of residues 1-11 of SEQ ID NO:3, addition of residue L before residue G1 and addition of residues YIRGR after residue V11) | 64.2 ± 5.5 | 2011 |
| 2 | PIP [56-71] | 15 | $^{56}$LGRVDIHVWDGVYIRG $^{71}$(variant of residues 1-11 of SEQ ID NO:3, addition of residue L before residue G1 and addition of residues YIRG after residue V11) | 62.8 ± 6.6 | 1855 |
| 3 | PIP [56-70] | 16 | $^{56}$LGRVDIHVWDGVYIR $^{70}$(variant of residues 1-11 of SEQ ID NO:3, addition of residue L before residue G1 and addition of residues YIR after residue V11) | 60.6 ± 4.5 | 1798 |
| 4 | PIP [56-69] | 17 | $^{56}$LGRVDIHVWDGVYI $^{69}$(variant of residues 1-11 of SEQ ID NO:3, addition of residue L before residue G1 and addition of residues YI after residue V11) | 59.8 ± 6.2 | 1642 |
| 5 | PIP [56-68] | 18 | $^{56}$LGRVDIHVWDGVY $^{68}$(variant of residues 1-11 of SEQ ID NO:3, addition of residue L before residue G1 and addition of residue Y after residue V11) | 61.6 ± 7.6 | 1528 |
| 6 | PIP [56-67] | 19 | $^{56}$LGRVDIHVWDGV $^{67}$(variant of residues 1-11 of SEQ ID NO:3, addition of residue L before residue G1) | 75.6 ± 2.7 | 1365 |
| 7 | PIP [57-67] | 20 | $^{57}$GRVDIHVWDGV $^{67}$(residues 1-11 of SEQ ID NO:3) | 65.1 ± 3.3 | 1252 |
| 8 | PIP [58-67] | 21 | $^{58}$RVDIHVWDGV $^{67}$(residues 2-11 of SEQ ID NO:3) | 29.4 ± 6.0 | 1195 |
| 9 | PIP [59-67] monomer | 7 | $^{59}$VDIHVWDGV $^{67}$(residues 3-11 of SEQ ID NO:3) | 34.2 ± 4.7 | 1039 |
| 10 | D60,65E PIP[59-67] | 8 | $^{59}$VEIHVWEGV $^{67}$(residues 1-9 of SEQ ID NO:2) | 5.4 ± 1.8 | 1067 |
| 11 | PIP [60-66] | 22 | $^{60}$DIHVWDG $^{67}$(residues 4-10 of SEQ ID NO:3) | 4.7 ± 2.6 | 841 |
| 12 | PIP [59-67] dimer | 1 | $^{59}$VDIHVWDGVVDIHVWDGV (SEQ ID NO:1) | 87.2 ± 3.7 | 2060 |

Figure 2:
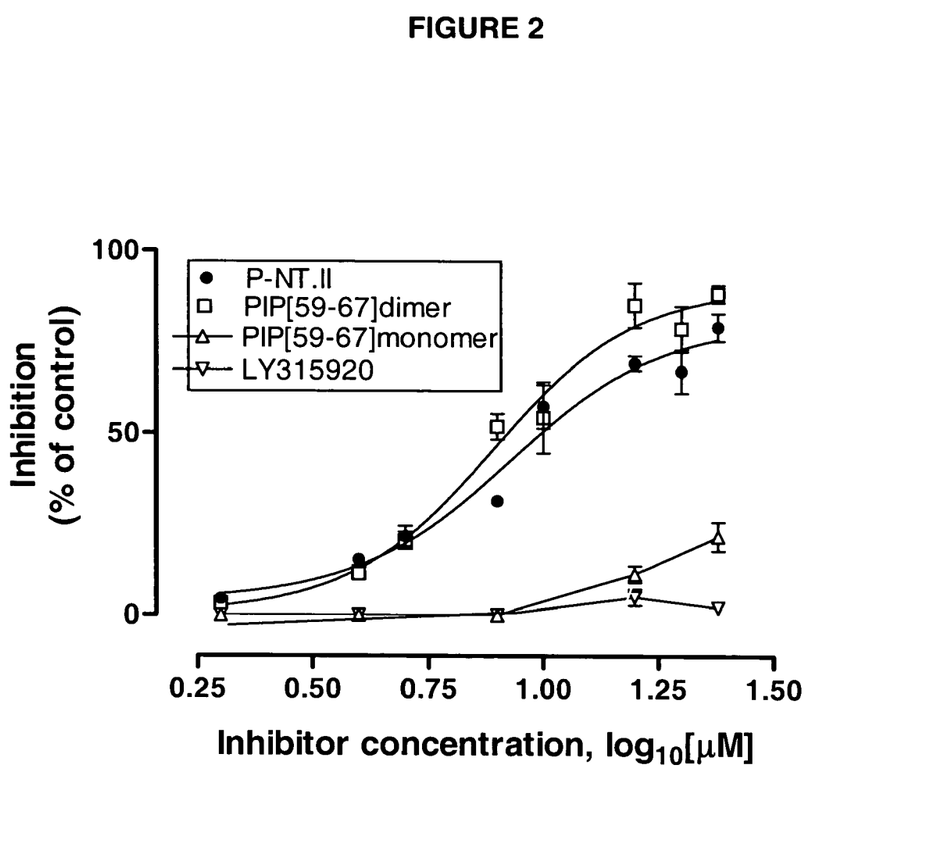
FIG. 2 shows the inhibition of collagenase 1 (MMP-1) activity by peptide analogues in comparison with that of the selective sPLA2 inhibitor LY 315920 indole analogue. Collagenase activity was assayed by collagen thin film method using collagen type II as substrate. $IC_{50}$ values were graphically determined from the inhibition curves, constructed on the basis of the in vitro results of collagenase assays. Results are the mean±SD of 3 separate experiments done in triplicates. (●), P-NT.II; (□), PIP [59-67] dimer; (Δ), PIP [59-67] monomer; (∇), LY 315920.
Figure 3A:
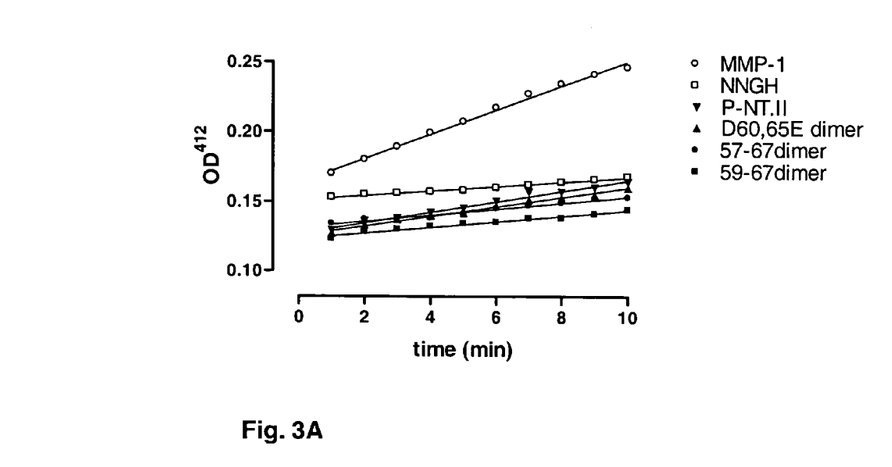
FIG. 3 illustrates the results of an assay on inhibition of human recombinant MMP-1 enzyme activity by various peptide mutants. (A) MMP-1 Activity Curves: The reaction velocity (V) was determined from the slope of the OD versus time (min) plot for each test inhibitor using the linear regression analysis. (○), Human recombinant MMP-1 purified enzyme; (□), NNGH standard positive control MMP-1 selective inhibitor; (▼), P-NT.II; (▲), D60,65E dimer; (●), PIP [57-67] dimer; (■), PIP [59-67] dimer. (B) MMP-1 Activity Inhibition Curves: Inhibition curves of various peptide mutants against the human MMP-1 activity. Results are expressed as the mean±SD (n=3).
Figure 3B:
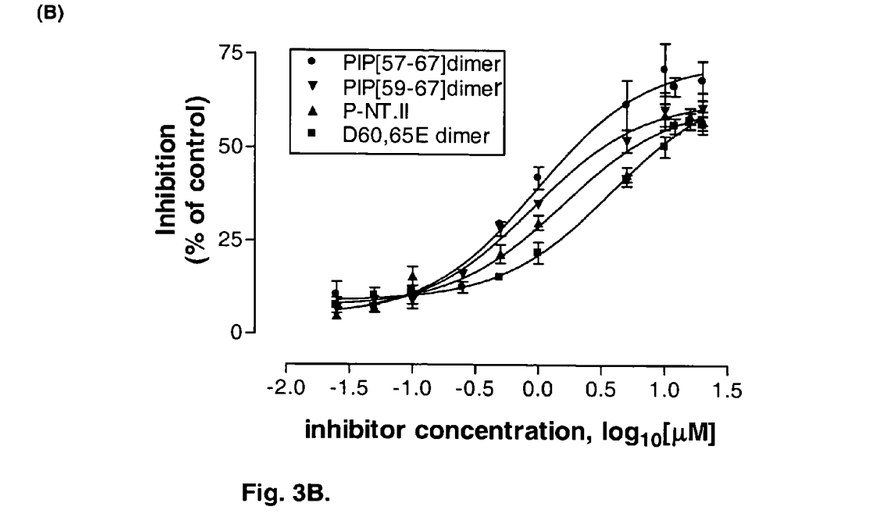

The results of collagenase I (MMP-1) inhibition assays (Table 3) indicate that the dimerized peptide mutant (PIP [59-67] dimer) is the most potent inhibitor amongst the family of analogues examined for MMP-inhibitory activity. The half maximal inhibition concentration, IC50 (mean±SD) was calculated as 8.43±1.17 and 7.75±1.11 μM, respectively, for P-NT.II and PIP [59-67] dimer (FIG. 2). specific test was subsequently used for further confirming the inhibitory activity of the most potent peptide (PIP [59-67] dimer) against human recombinant MMP-1 in comparison with that of the other mutant peptides. Inhibition of human recombinant MMP-1 enzyme activity by various peptide mutants is shown in FIG. 3. Using the linear regression analysis, the reaction velocity (V) was determined from the slope of the OD versus time (min) plot for each test inhibitor (FIG. 3A). MMP-1 selective inhibitor NNGH was included in the assay as a positive control. Among those peptide analogues having stronger anti-collagenase I activity (Table 3B), PIP [59-67] dimer exhibited the strongest inhibition against the recombinant human purified MMP-1 activity (FIG. 3B, Table 4), thus confirming the results obtained with the initial screening assays using collagen thin film as a substrate and collagenase 1 as an enzyme.

TABLE 4

IC50 values of peptide mutants against human recombinant MMP-1 activity.

| Peptide | IC$_{50}$ (μM) | ±SD |
| --- | --- | --- |
| P-NT.II | 1.548 | 0.651 |
| D60, 65E-PIP[59-67] dimer | 3.738 | 1.222 |
| PIP [59-67] dimer | 0.9017 | 0.596 |
| PIP [57-67] dimer | 0.9695 | 0.632 |

Figure 4:
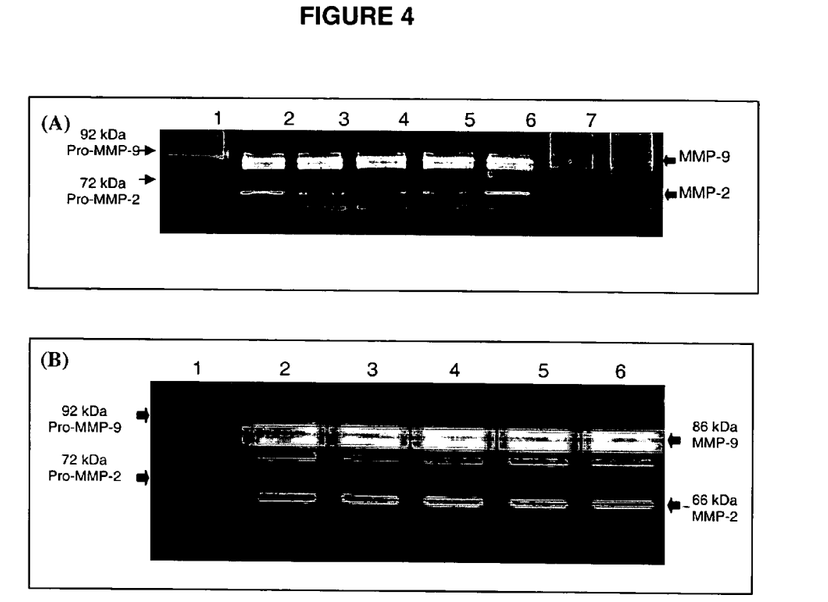
Figure 5:
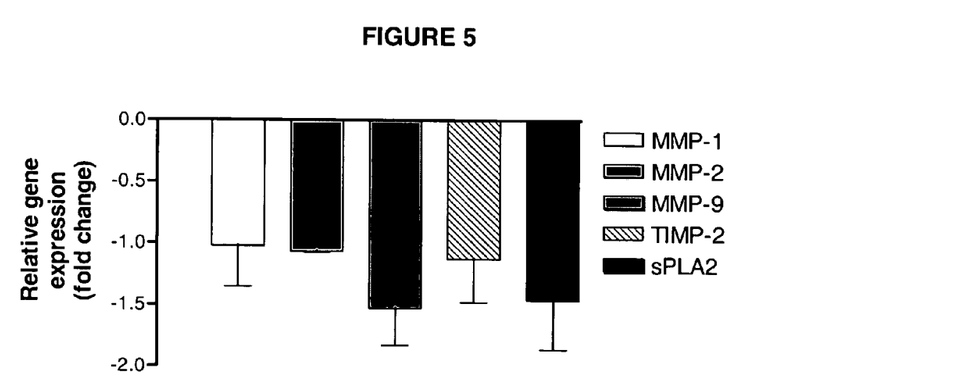
FIG. 5 is a view of the effect of peptide on the relative expression of MMP and sPLA2 genes. QRT-PCR was used for assessing relative mRNA expression levels of IL-1β-stimulated rabbit synovial fibroblast cells in the presence and absence of the candidate lead peptide PIP [59-67] dimer. The amount of each mRNA was obtained by quantitative RT-PCR. The relative levels of gene expression were normalized to the housekeeping gene (GAPDH). Results showed that co-treatment with the peptide significantly inhibited the IL-1β induced expression of MMP-1, MMP-2, MMP-9, TIMP-2 and sPLA2 genes from the cultured rabbit synovial fibroblasts. Values are expressed as ±S.E.

Since matrix metalloproteinases (MMPS) play key roles in matrix remodeling processes that are essential for tumor growth and invasion [24], we examined the peptide candidate PIP [59-67] dimer for inhibition against the activity of gelatinases (MMP-2 and MMP-9) secreted by the rabbit synovial fibroblast cells upon stimulation by the cytokine IL-1β. Gelatin zymography of the concentrated supernatants from the culture showed that increasing doses of PIP [59-67] dimer (1-10 μM) failed to inhibit the activity of MMP-2 and MMP-9 (FIG. 4B). Further densitometric analysis of the zymograms indicated that the activity of secreted MMP-2 and MMP-9 in culture media was not significantly reduced by treatment with various doses (1-10 μM) of PIP [59-67] dimer as compared to untreated control fibroblast cells. These data clearly demonstrate that PIP [59-67] dimer does not reduce the gelatinolytic activities of secreted MMP-2 and MMP-9 in treated fibroblast cells. In order to examine the potential suppression of sPLA2 and MMP gene expression by the candidate peptide, we used QRT-PCR for assessing relative mRNA expression levels of IL-1β induced rabbit synovial fibroblasts in the presence and absence of the inhibitor peptide dimer. When the IL-1β-induced fibroblasts cells were treated with 5 μM of the peptide, the levels of the (MMP-1, -2, -9, TIMP-1 and sPLA2) gene transcripts were significantly suppressed (FIG. 5).

Since the levels of secreted MMP-2 and MMP-9 activity as measured by gelatin zymography are not significantly reduced (FIG. 4B), PIP [59-67] dimer does not appear to directly inhibit secreted MMP-2 or MMP-9 activity. Moreover, when the samples of human synovial fluid containing MMP-2 and -9 (FIG. 1) or the secreted MMP-2 and -9 in cultured synovial fibroblasts (FIG. 4A) were co-incubated in vitro with the peptides for 1 h and subjected to gelatin zymography, the results indicate that the inhibition of MMP-2 and -9 gelatinase activities by the peptide dimer is insignificant. From these results, it is evident that the peptide dimer acts against the gelatinases (MMP-2 and MMP-9) mainly through the downregulation of the expression of genes encoding for MMP-2 and MMP-9, rather than directly inhibiting the enzymatic activity of the gelatinases secreted by the fibroblasts (FIG. 5). In contrast, this peptide acts against collagenase 1 (MMP-1) through suppression of its gene expression (FIG. 5) and by directly inhibiting its enzyme activity (Table 4). These results provide strong in vitro evidence for control and modulation of enzyme activity and transcription of both MMP-1 and sPLA$_2$. Since the initial cleavage of collagen by collagenase (MMP-1) is the critical irreversible step leading to the abnormalities observed in the disease state, this invention provides new therapeutic options in the treatment of arthritis and cancer.

It will be understood that the invention has been described by way of example only and modifications may be made whilst remaining within the scope and spirit of the invention.

REFERENCES CITED

1. Murakami M, Kudo I. (2002) Phospholipase A2. *J. Biochem.* (Tokyo). 131, 285-92.
2. Cirino G. et al. (1994) Recombinant secreted nonpancreatic phospholipase A2 induces a synovitis-like inflammation in the rat air pouch. *J Rheumatol.* 21, 824-29.
3. Jamal O S. et al. (1998) Increased expression of human type IIa secretory phospholipase A2 antigen in arthritic synovium. *Ann Rheum Dis.* 57, 550-58.
4. Lin M K. et al. (1998) Induction of secretory phospholipase A2 confirms the systemic inflammatory nature of adjuvant arthritis. *Inflammation* 22, 161-73.
5. Jiang J, et al. (2002) Expression of group IIA secretory phospholipase A2 is elevated in prostatic intraepithelial neoplasia and adenocarcinoma. *Am J Pathol.* 160(2): 667-71.
6. Graff J R et al. (2001) Expression of group IIa secretory phospholipase A2 increases with prostate tumor grade. *Clin Cancer Res.* 7(12):3857-61.
7. Xu X C. (2002) COX-2 inhibitors in cancer treatment and prevention, a recent development. *Anticancer Drugs.* 13(2):127-37. Review.
8. Gopalakrishnakone P., Thwin M M. et al. (2002) Novel Therapeutic and Prophylactic Agents and Methods of Using Same. U.S. patent application Ser. No. 10/163, 499 (US Filing date: 7 Jun. 2002).
9. Thwin M M et al. (2000) Recombinant antitoxic and antiinflammatory factor from the nonvenomous snake Python reticulatus: phospholipase A2 inhibition and venom neutralizing potential. *Biochemistry.* 39(31):9604-11.
10. Thwin M M et al. (2002) Functional site of endogenous phospholipase A2 inhibitor from python serum. *Eur J Biochem.* 269(2):719-27.
11. Thwin M M et al. (2004) Effect of phospholipase A2 inhibitory peptide on inflammatory arthritis in a TNF transgenic mouse model: a time-course ultrastructural study. *Arthritis Res Ther.* 6(3):R282-94. Epub Apr. 28, 2004.
12. Thwin M M et al. (2003) Secretory phospholipase A2 activity in the normal and kainate injected rat brain, and inhibition by a peptide derived from python serum. *Exp Brain Res.* 150(4):427-33. Epub Apr. 18, 2003.
13. Gopalakrishnakone P, Thwin M M, Ong W Y, Sato K. (2004) Phospholipase A2-inhibitory peptide with antiarthritic and neuroprotective activities. U.S. patent application Ser. No. 10/836,825 INTRO Ref.: GOPAL P 08-US, Filing Date: 30 Apr. 2004.
14. Clark I M. et al. (2000) Matrix metalloproteinase inhibitors in the treatment of arthritis. *Curr Opin Antiinflammatory Immunomodulatory Invest Drugs* 2, 16-25.
15. Konttinen Y T. et al. (1999) Analysis of 16 different matrix metalloproteinases (MMP-1 to MMP-16) in the synovial membrane: different profiles in trauma and rheumatoid arthritis. *Ann Rheum Dis.* 58, 691-97.
16. Borkakoti N (2004) Matrix metalloprotease inhibitors: design from structure. *Biochem. Soc. Trans.* 32, 17-20.
17. Pardo A, Selman M. (2005) MMP-1: the elder of the family. Review. *Int J Biochem Cell Biol.* 37(2), 283-8.
18. Mook O R. et al. (2004) The role of gelatinases in colorectal cancer progression and metastasis. Review. *Biochim Biophys Acta.* 1705(2), 69-89.

19. Borkakoti. N. (2004) Matrix metalloprotease inhibitors: design from structure. *Biochemical Society Transactions* Volume 32, part 1.
20. Bachmeier B E et al. (2005) Matrix metalloproteinases in cancer: comparison of known and novel aspects of their inhibition as a therapeutic approach. *Expert Rev Anticancer Ther.* 5(1), 149-63.
21. Kolomytkin O V, et al. (2002) IL-1beta-induced production of metalloproteinases by synovial cells depends on gap junction conductance. *J Physiol Cell Physiol* 282(6):C1254-C1260.
22. Livak K J, Schmittgen T D. (2001) Analysis of relative gene expression data using real-time quantitative PCR and the 2(-Delta Delta C(T)) Method. *Methods* 25(4): 402-8.
23. Snyder D W. et al. (1999) Pharmacology of LY315920/S-5920, [[3-(aminooxoacetyl)-2-ethyl-1-(phenylmethyl)-1H-indol-4-yl]oxy]acetate, a potent and selective secretory phospholipase A2 inhibitor: A new class of anti-inflammatory drugs, SPI. *J Pharmacol Exp Ther.* 288(3):1117-24.
24. Johansson N, Ahonen M, Kahari V M. (2000) Matrix metalloproteinases in tumor invasion. *Cell Mol Life Sci.* 57(1):5-15. Review.
25. Bazan N G, Colangelo V, Lukiw W J. (2002) Prostaglandins and other lipid mediators in Alzheimer's disease. *Prostaglandins Other Lipid Mediat.* 68-69:197-210.

CITED US PATENT FILINGS

1. Gopalakrishnakone P, Thwin M M, Ong W Y, Sato K. (2004) Phospholipase A2-inhibitory peptide with anti-arthritic and neuroprotective activities. U.S. patent application Ser. No. 10/836,825 INTRO Ref.: GOPAL P 08-US, Filing Date: 30 Apr. 2004.
2. GoPalakrishnakone P, Thwin M M, Jeyaseelan K, Armugam A. (2002) Novel therapeutic and prophylactic agents and methods of using same. U.S. Patent Ser. No. 10/163,499, Filing Date: 7 Jun. 2002. United States Patent Publication No. US 2003/0027764A1 (publication date: Feb. 6, 2003).

SEQUENCE LISTING

```
<160> NUMBER OF SEQ ID NOS: 6

<210> SEQ ID NO 1
<211> LENGTH: 18
<212> TYPE: PRT
<213> ORGANISM: Python reticulatus
<220> FEATURE:
<221> NAME/KEY: MISC_FEATURE
<222> LOCATION: (1)..(18)
<223> OTHER INFORMATION: 18-residue dimer peptide designated PIP [59-67]
      dimer
<300> PUBLICATION INFORMATION:
<301> AUTHORS: Thwin, M.-M. et al.
<303> JOURNAL: Biochemistry
<304> VOLUME: 39
<306> PAGES: 9604-9611
<307> DATE: 2000
<308> DATABASE ACCESSION NUMBER: AAF73945
<309> DATABASE ENTRY DATE: 2000-06-02
<313> RELEVANT RESIDUES: (1)..(18)

<400> SEQUENCE: 1

Val Asp Ile His Val Trp Asp Gly Val Val Asp Ile His Val Trp Asp
1               5                   10                  15

Gly Val

<210> SEQ ID NO 2
<211> LENGTH: 18
<212> TYPE: PRT
<213> ORGANISM: Python reticulatus
<220> FEATURE:
<221> NAME/KEY: MISC_FEATURE
<222> LOCATION: (1)..(18)
<223> OTHER INFORMATION: 18-residue dimer peptide designated D60,65E-PIP
      [59-67] dimer
<300> PUBLICATION INFORMATION:
<301> AUTHORS: Thwin, M.-M. et al.
<303> JOURNAL: Biochemistry
<304> VOLUME: 39
<306> PAGES: 9604-9611
<307> DATE: 2000
<308> DATABASE ACCESSION NUMBER: AAF73945.1
<309> DATABASE ENTRY DATE: 2000-06-02
<313> RELEVANT RESIDUES: (1)..(18)

<400> SEQUENCE: 2
```

```
Val Glu Ile His Val Trp Glu Gly Val Val Glu Ile His Val Trp Glu
1               5                   10                  15

Gly Val

<210> SEQ ID NO 3
<211> LENGTH: 22
<212> TYPE: PRT
<213> ORGANISM: Python reticulatus
<220> FEATURE:
<221> NAME/KEY: MISC_FEATURE
<222> LOCATION: (1)..(22)
<223> OTHER INFORMATION: 22-residue dimer peptide designated PIP [57-67]
      dimer
<300> PUBLICATION INFORMATION:
<301> AUTHORS: Thwin, M.-M. et al.
<303> JOURNAL: Biochemistry
<304> VOLUME: 39
<306> PAGES: 9604-9644
<307> DATE: 2000
<308> DATABASE ACCESSION NUMBER: AAF73945.1
<309> DATABASE ENTRY DATE: 2000-06-02
<313> RELEVANT RESIDUES: (1)..(22)

<400> SEQUENCE: 3

Gly Arg Val Asp Ile His Val Trp Asp Gly Val Gly Arg Val Asp Ile
1               5                   10                  15

His Val Trp Asp Gly Val
            20

<210> SEQ ID NO 4
<211> LENGTH: 27
<212> TYPE: DNA
<213> ORGANISM: Python reticulatus
<220> FEATURE:
<221> NAME/KEY: misc_feature
<222> LOCATION: (285)..(311)
<223> OTHER INFORMATION: DNA Sequence of SEQ ID No.1
<300> PUBLICATION INFORMATION:
<308> DATABASE ACCESSION NUMBER: AAF73945.1
<309> DATABASE ENTRY DATE: 2000-06-02
<313> RELEVANT RESIDUES: (285)..(311)

<400> SEQUENCE: 4
gttgacatac atgtttggga tggagtg                                              27

<210> SEQ ID NO 5
<211> LENGTH: 27
<212> TYPE: DNA
<213> ORGANISM: Python reticulatus
<220> FEATURE:
<221> NAME/KEY: misc_feature
<222> LOCATION: (285)..(311)
<223> OTHER INFORMATION: DNA Sequence of SEQ ID No.2
<300> PUBLICATION INFORMATION:
<308> DATABASE ACCESSION NUMBER: AAF73945.1
<309> DATABASE ENTRY DATE: 2000-06-02
<313> RELEVANT RESIDUES: (285)..(311)

<400> SEQUENCE: 5
gttgaaatac atgtttggga tggagtg                                              27

<210> SEQ ID NO 6
<211> LENGTH: 33
<212> TYPE: DNA
<213> ORGANISM: Python reticulatus
<220> FEATURE:
<221> NAME/KEY: misc_feature
<222> LOCATION: (279)..(311)
<223> OTHER INFORMATION: DNA Sequence of SEQ ID No.3
```

```
<300> PUBLICATION INFORMATION:
<308> DATABASE ACCESSION NUMBER: AAF73945.1
<309> DATABASE ENTRY DATE: 2000-06-02
<313> RELEVANT RESIDUES: (279)..(311)

<400> SEQUENCE: 6
ggccgtgttg acatacatgt ttgggatgga gtg                                33
``` what is claimed is:

1. A composition comprising an 18-residue polypeptide set forth as SEQ ID NO:1.
2. A composition comprising an 18-residue polypeptide set forth as SEQ ID NO:2.
3. A composition comprising a 22-residue polypeptide set forth as SEQ ID NO:3.
4. The composition of claim 1 that contains a pharmaceutically acceptable carrier.
5. A method for treatment of an inflammatory condition, comprising administering to a patient in need of such treatment a composition of claim 4 comprising a therapeutically effective dose of said polypeptide.
6. The method of claim 5 wherein the inflammatory condition is rheumatoid arthritis.
7. The composition of claim 2 that contains a pharmaceutically acceptable carrier.
8. The composition of claim 3 that contains a pharmaceutically acceptable carrier.
9. A method for treatment of an inflammatory condition, comprising administering to a patient in need of such treatment a composition of claim 7 comprising a therapeutically effective dose of said polypeptide.
10. A method for treatment of an inflammatory condition, comprising administering to a patient in need of such treatment a composition of claim 8 comprising a therapeutically effective dose of said polypeptide.
11. The method of claim 9 wherein the inflammatory condition is rheumatoid arthritis.
12. The method of claim 10 wherein the inflammatory condition is rheumatoid arthritis.

* * * * *